(12) United States Patent
Delapierre et al.

(10) Patent No.: US 9,588,084 B2
(45) Date of Patent: Mar. 7, 2017

(54) DEVICE FOR DETECTING GASES AND/OR VOLATILE ORGANIC COMPOUNDS (VOC)

(75) Inventors: Guillaume Delapierre, Vif (FR);
Yanxia Hou-Broutin, Bilieu (FR);
Heather McCaig, Pasadena, CA (US);
Edward Myers, Sherman Oaks, CA (US); Michael L. Roukes, Pasadena, CA (US)

(73) Assignees: California Institute of Technology, Pasadena, CA (US); Commissariat a L'Energie Atomatique Et Aux Energies Alternatives, Paris (FR)

( * ) Notice: Subject to any disclaimer, the term of this patent is extended or adjusted under 35 U.S.C. 154(b) by 1121 days.

(21) Appl. No.: 13/497,962

(22) PCT Filed: Sep. 24, 2010

(86) PCT No.: PCT/IB2010/002633
§ 371 (c)(1),
(2), (4) Date: Oct. 31, 2012

(87) PCT Pub. No.: WO2011/036565
PCT Pub. Date: Mar. 31, 2011

(65) Prior Publication Data
US 2013/0043143 A1 Feb. 21, 2013

Related U.S. Application Data

(60) Provisional application No. 61/245,998, filed on Sep. 25, 2009.

(30) Foreign Application Priority Data

Sep. 25, 2009 (FR) ...................................... 09 04589

(51) Int. Cl.
G01N 27/30 (2006.01)
G01N 29/036 (2006.01)
G01N 29/02 (2006.01)

(52) U.S. Cl.
CPC ......... *G01N 29/036* (2013.01); *G01N 29/022* (2013.01); *G01N 2291/0255* (2013.01);
(Continued)

(58) Field of Classification Search
CPC .... G01N 27/404–27/407; G01N 27/41; G01N 27/4045; G01N 27/4074;
(Continued)

(56) References Cited

U.S. PATENT DOCUMENTS 5,607,573 A 3/1997 Miller et al.
2004/0040841 A1 3/2004 Gonzalez-Martin et al.
(Continued)

FOREIGN PATENT DOCUMENTS

FR 2815351 4/2002

OTHER PUBLICATIONS

Brooksby et al., Langmuir, 2005, 21, 1672-1675.*
(Continued)

*Primary Examiner* — Gurpreet Kaur
(74) *Attorney, Agent, or Firm* — Gates & Cooper LLP

(57) ABSTRACT

The present invention concerns a device for detecting gases or volatile organic compounds (VOC) comprising an electrically conducting or semiconducting zone functionalized with an organic film resulting from the polymerization of aromatic diazonium salt derived monomer.

13 Claims, 4 Drawing Sheets

Figure 1:
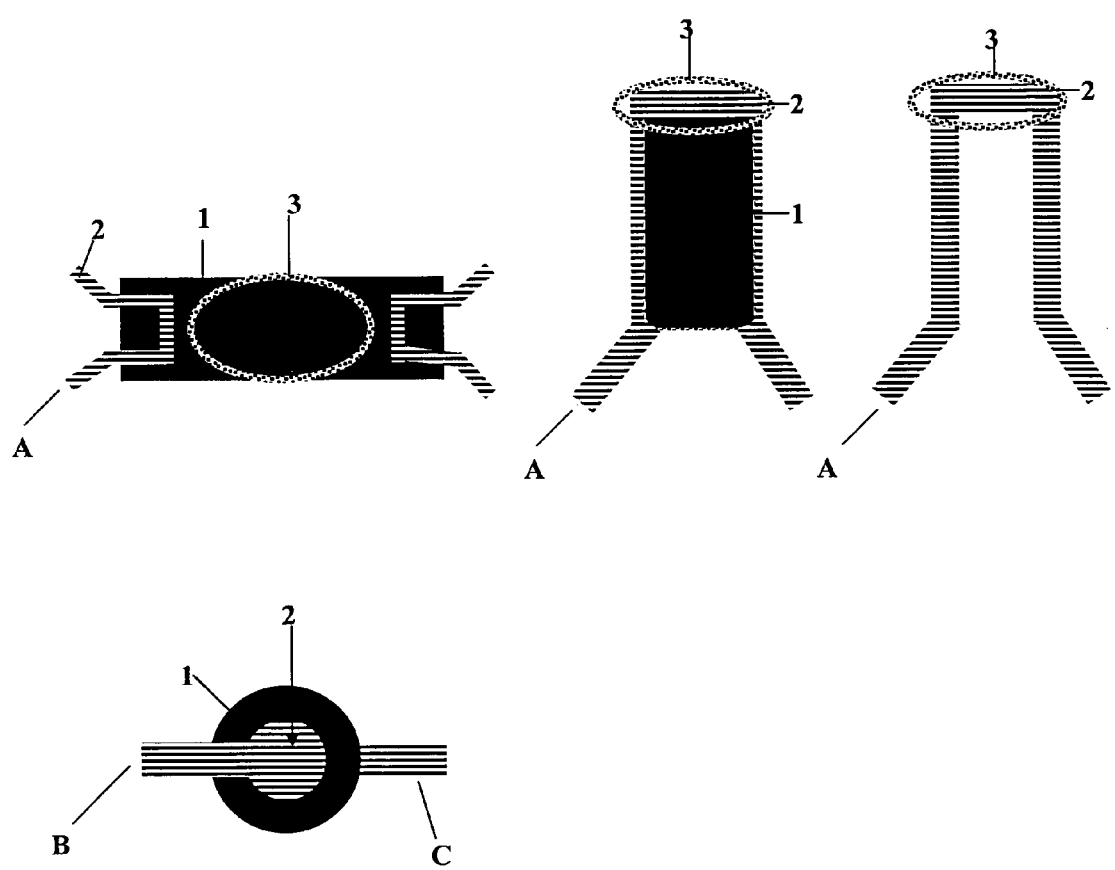

(52) U.S. Cl.
CPC ............... *G01N 2291/0256* (2013.01); *G01N 2291/0426* (2013.01)

(58) Field of Classification Search
CPC ............... G01N 29/022; G01N 29/036; G01N 229/0426; Y02T 10/44; Y02T 10/47
See application file for complete search history.

(56) References Cited

U.S. PATENT DOCUMENTS

| | | | | |
|---|---|---|---|---|
| 2005/0042758 | A1* | 2/2005 | Zyhowski | G01N 31/22 436/3 |
| 2006/0099715 | A1* | 5/2006 | Munoz et al. | 436/151 |
| 2012/0272742 | A1* | 11/2012 | Andreucci et al. | 73/778 |

OTHER PUBLICATIONS

Wen et al. Sensors and Actuators, 2007, 422-427.*
Anariba et al. Anal. chem, 2003, 75, 3837-3844.*
Li et al. Nature Nanotechnology, 2007, 114-120.*
Liu et al.: "Diazonium salts: Stable monolayers on gold electrodes for sensing applications", Journal of Electroanalytical Chemistry, vol. 600, No. 2, Jan. 26, 2007, pp. 335-344.
Gooding, Justin J.: "Advances in Interfacial Design for Electrochemical Biosensors and Sensors: Aryl Diazonium Salts for Modifying Carbon and Metal Electrodes", Electroanalysis, vol. 20, No. 6, Feb. 13, 2008, pp. 573-582.
Tessier et al.: "Surface Electroinitiated Emulsion Polymerization (SEEP): A Mechanistic Approach", Chemistry of Materials, vol. 21, No. 18, Aug. 24, 2009, pp. 4261-4274.
Polsky et al.: "Multifunctional Electrode Arrays: Towards a Universal Detection Platform", Electroanalysis, vol. 20, No. 6, Feb. 13, 2008, pp. 671-679.
International Search Report for PCT Application No. PCT/IB/002633 filed on Sep. 24, 2010.
McGill, R. A., "Choosing polymer-coatings for chemical sensors," Chemtech 24(9), pp. 27-37 (1994).
James, D., et al., "Chemical Sensors for Electronic Nose Systems", Michrochimica Acta 149, pp. 1-17 (2005).
Jun, H.-K., et al., "Electrical properties of polypyrrole gas sensors fabricated under various pretreatment conditions", Sensors and Actuators B 96 (2003), pp. 576-581.
Lim, C., et al., "Simultaneous and Wireless Measurement of CO2 and NO2 using a SAW Reflective Delay Line", The 15th International Conference on Solid State Sensors, Actuators, and Microsystems, IEEE, Transducers, Denver, pp. 995-998, Jun. 21-25, 2009.

* cited by examiner

QCM n°1 (function -NO₂)

QCM n°2 (function -Br)

DEVICE FOR DETECTING GASES AND/OR VOLATILE ORGANIC COMPOUNDS (VOC)

The present invention relates to a device for detecting gases and/or volatile organic compounds (VOC), a process for the preparation of such a device, and a process for detecting gases and/or volatile organic compounds (VOC).

Environmental pollutions have greatly increased during the last few decades, the volatile organic compounds (VOC) having been recognized as the main cause of sick house syndrome. Indeed, they can cause or aggravate certain conditions including allergies, asthma, cancer and emphysema. Consequently, needs and interests exist for the development of effective sensors capable of detecting directly a large number of gases and/or volatile organic compounds (VOC).

The article of D. James et al., Michrochimica Acta 149, 1-17 (2005) describes systems used for odour analysis, also called "electronic noses". These systems used chemical sensors which are transducers incorporating chemical interactions into electrical signals. These "electronic noses" are used for applications ranging from the food industry to the medical industry, and also including the environmental monitoring and the process control. These gas sensors operate by binding molecules to the device surface through one or more mechanisms including adsorption, absorption, or chemisorption. The binding mechanism has important implications for the selectivity and reversibility of the sensing system, as a high binding strength will result in poor reversibility. Thus, weaker adsorptive interactions are preferred for good reversibility, but with a poor selectivity as a consequence. As high selectivity with high reversibility is difficult to attain, a compromise is necessary.

Some other current devices for detecting gases use sensors comprising a pair of electrodes coated with organic materials, like polymers, deposited on and between the electrodes in order to produce an electrical connection between the electrodes. The organic polymers used are sensitive to the presence of gases, to the extent that adsorption of the gases onto the polymer surfaces affects the electrical properties of the polymers. Hence, the presence of a gas may be detected by monitoring, for example, the change in resistance or resonance frequency of the sensor exposed to said gas. Indeed, these sensor technologies employ thin sorbent layers of chemically selective material to collect molecules of interest at the interphase of the coated sensor, said chemically selective materials allowing a direct detection of the gases and/or volatile organic compounds (VOC).

Other detecting gas sensors are the piezoelectric sensors, based on the phenomena by which certain anisotropic crystals, when subjected to mechanical stress, generate electric dipoles. Many different forms of piezoelectric sensors exist, like bulk acoustic wave (BAW) sensors or surface acoustic wave (SAW) sensors. The bulk acoustic wave (BAW) sensors are also commonly referred to as quartz crystal microbalance (QCM). These sensors are very sensitive mass deposition sensors based on the piezoelectric properties of the quartz crystal. This technique uses the changes in resonance frequency of the crystal to measure the mass on the surface as the resonance frequency is highly dependent on any changes of the crystal mass. The quartz crystal microbalances (QCM) generally comprised electrodes attached to the quartz, said electrodes exerting an alternating current which forces the crystal to oscillate with a fundamental frequency. These sensors can be used in liquid environments for determining the affinity of molecules to surfaces functionalized with recognition sites. These sensors consist of a thin piezoelectric plate with electrodes onto both sides, a voltage across the electrodes being applied and inducing a shear deformation and vice-versa. As the electrodes are attached to either side of the crystal the wave produced travels though the bulk of the material. The crystal is generally coated with a chemical layer allowing the extraction of analytes from test samples. The principle of sensing is that the change in device frequency is proportional to the mass of material deposited upon the crystal. However, it appears that the chemical layers of these gas sensors are influenced by humidity, and changes in room temperature can have an effect on both the crystal and its polymer coating.

The piezoelectric gas sensors described in the prior art are only adapted to the detection of specific gases, but they do not allow the simultaneous detection of various types of gas.

For example, the resonant sensor based on quartz crystal microbalance (QCM) and $BaCO_3$ of Seh et al. (Sensors and Actuators B 108 (2005), 547-552) is only sensitive to $NO_2$ at a temperature of 300° C., $BaCO_3$ reacting with $NO_2$ to form $Ba(NO_3)_2$.

Lim et al. (Transducers 2009, Jun. 21-25, 2009) describe a wireless surface acoustic wave (SAW) chemical sensor for simultaneous measurement of only $CO_2$ and $NO_2$ on a 41° YX $LiNbO_3$ piezoelectric substrate. The developed sensor consists of a SAW reflective delay lines structured by an interdigital transducer (IDT), reflectors, a Teflon AF 2400 film (a $CO_2$ sensitive film) and an Indium Tin Oxide (ITO) film (a $NO_2$ sensitive film). Nevertheless, the fabrication procedure of such gas sensor involves numerous steps: deposition of an aluminium film using electron beam evaporator, wet-etching of the aluminium in an acidic solution, deposition of a PMMA film and of an ITO film by DC magnetron sputter, elimination of the passivation layer (PMMA), and deposition of a gold layer onto the substrate, prior to Teflon AF 2400 film deposition.

The article of A. McGill et al., Chemtech, Sep. 2004, 27-37 describes surface acoustic wave (SAW) chemical sensors, these sensors being coated with polymers applied by spray coating or by soaking. However, these methods do not allow the functionalization of selective parts of the sensor, in small dimensions. Moreover, this article discloses specific polymers, like the polymer family of polysiloxanes, and it appears that one of the drawbacks of this type of polymer is the polysiloxanes' poor wetting properties on surface acoustic wave (SAW) devices.

According to the type of detection desired, the nature of the sensitive polymer is adapted. For example, the article of H.-K Jun et al., Sensors and Acturators B 96 (2003) 576-581, discloses the use of conducting polymers such as polypyrrole, polyaniline and polythiophene, these polymers being commonly regarded as sensing materials due to their gas sensing ability and their optimum performances at room temperature. However, the major drawbacks of these kinds of sensors are their very fragile structure, and their tendency to oxidize. Indeed, the sensor coatings are prepared by chemical oxidation, this reaction often leading to the oxidation and deactivation of the electrically conducting surface of the gas sensor. Besides, these conducting polymers are immobilized at the surface of the gas sensor without establishing a covalent linkage, which leads to poor resistant organic films.

Clearly the devices for detecting gases and/or volatile organic compounds (VOC) known from the prior art are not sufficiently sensitive to such a broad range of gases, and none of these prior art documents does provide a satisfactory solution concerning the problem of surface sensor oxidation.

The present invention overcomes the inadequacies and disadvantages of the devices described in the state of the art by using the properties of an insulating polymer based on aromatic diazonium salt derived polymer fulfilling the role of sensitive coat gas sensor. Indeed, the present invention provides a specific device for detecting gases and/or volatile organic compounds (VOC) comprising at least one aromatic diazonium salt derived polymer electro-grafted at the surface of the gas sensor, this specific device showing an excellent compromise of performances.

Thus, the device of the present invention allows:
the functionalization of only small dimensions (only some nm) of some specific parts of the surface of the sensor implemented,
the functionalization of the sensor with polymers bearing different kinds of chemical functions, each of these chemical functions having a particular sensitivity with a specific gas (modification of the affinity of the surface of the sensor according to the gas to detect),
the modulation of the thickness of the polymer coated on the sensor, in order to control the interaction between the polymer and the gas to detect,
the formation of a solid covalent link between the aromatic diazonium salt derived polymer and the surface of the gas sensor, which is particularly advantageous for gas sensors comprising mobile parts and needing more resistant organic films.

The specific device of the present invention is particularly suitable for detecting potential pollutants, such as $NH_3$, $CO_2$, CO, $NO_x$, $H_2S$ or $Cl_2$, under atmospheric conditions, and also organic molecules present in their vapour state, such as solvents like ethanol, hexane, toluene, ethyl acetate.

The first subject-matter of the present invention is a device for detecting gases and/or volatile organic compounds (VOC) comprising a gas sensor coated with a specific organic film.

A second subject-matter of the present invention is a process for the preparation of the device of the present invention.

The last subject-matter of the present invention is a process for detecting gases and/or volatile organic compounds (VOC), involving the specific device of the present invention.

The chemical processes governing the sensitivity and selectivity of a polymer coated gas sensor are very similar to those of the solution process of a vapour in a liquid solvent. When a solvent is exposed to a vapour, vapour molecules distribute themselves between the gas and liquid phases, and a thermodynamic equilibrium is set up. The ratio between the concentration of the vapour in the gaseous phase $C_v$ and the concentration of the polymer in the liquid phase $C_p$ is the partition coefficient $K_p$:

$$K_p = C_p/C_v$$

The partition coefficient measures the overall strength of interactions between the polymer and the vapour, and for high values of $K_p$, vapour sorption is stronger.

The device for detecting gases and/or volatile organic compounds (VOC) of the present invention comprises transduction means and a gas sensor. The transduction means comprise means for applying electrical signals to the sensor and detection means for detecting a chosen electrical signal in the presence of a gas, and more specifically the transduction means comprise electrical connexions to the gas sensor, a measuring apparatus and a computer.

The gas sensor of the present invention can be a sensing instrument that utilizes resonant mechanical motion to transducer added mass on its surface into an electrical signal, and more particularly, the gas sensor of the present invention can be selected from the surface acoustic wave (SAW) sensors, the bulk surface wave (BAW) sensors also commonly referred to as the quartz crystal microbalances (QCM), the Micro ElectroMechanical System (MEMS) sensors and the Nano ElectroMechanical System (NEMS) sensors.

The gas sensor of the present invention generally operates at frequencies comprised from 1 to 200 MHz.

The surface of the pair of electrodes of said gas sensor of the present invention comprises at least one electrically conducting and/or semiconducting zone functionalized with at least one organic film resulting from the polymerization of at least one aromatic diazonium salt derived polymer corresponding to the following formula:

$$m((R)_n Ar-N_2^+) X^{m-} \quad (I)$$

in which:
X— is an anion,
Ar is an aryl group which can be mono-, di- or trisubstituted with identical or different —R groups,
R is selected from hydrogen atom, linear or branched aliphatic radicals comprising from 1 to 30 carbon atoms, aromatic radicals comprising 5 or 6 carbon atoms and possibly 1 to 3 heteroatoms chosen from —N, —O or —S, halogen atoms, carboxyl, nitro, amino, amido, cyano groups, alkoxy or alkoxycarbonyl groups comprising from 1 to 3 alkoxy units, the preferred substituents R being selected from the —Br, —COOH, —NO$_2$, —OCH$_3$, —CONH$_2$ and —OCH$_3$ groups,
m is equal to 1, 2 or 3, and
n is equal to 1, 2 or 3.

By aromatic group, is meant, according to the present invention aryl, benzyl, pyrrole or thiophenyl group for example.

In a preferred embodiment of the present invention, the anion X— is chosen from Cl—, Br—, I—, $HSO_4$—, $ClO_4$—, $BF_4$—, $PF_6$—, $CH_3C_6H_4SO_3$—, $ZnCl_4^{2-}$, and $Fe(CN)_6^{3-}$, and preferably from $BF_4$—, $PF_6$—, and $ZnCl_4$—.

Here-below are represented the formulae of some aromatic diazonium salts, which can be used within the framework of the present invention.

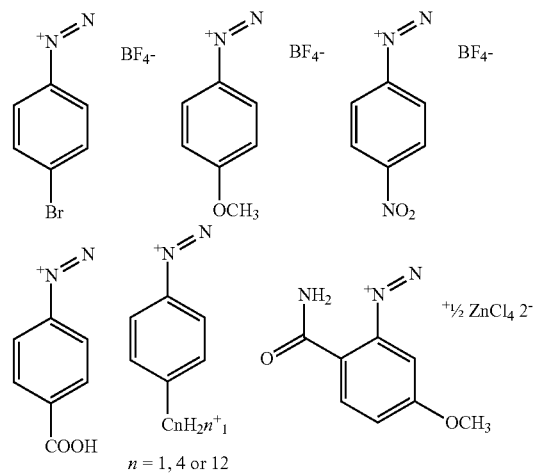

-continued

[structures with Cl⁻, diazonium, OCH₃, morpholine, ZnCl₂, and biphenyl diazonium with OCH₃ groups]

The more preferred aromatic diazonium salts according to the present invention are the 4-nitrophenyl diazonium salt, the 4-bromophenyl diazonium salt, the 4-methoxyphenyl diazonium salt and the fast blue red salt.

The aromatic diazonium salt can be a commercial product, or it can be synthetized if a specific interaction is needed. In order to vary the selectivity of the sensitive layer of the gas sensor, it is possible to formulate the diazonium salt derived polymer by adding specific organic molecules, or by copolymerizing said diazonium salt with another polymer.

The surface of the pair of electrodes of said gas sensor comprises at least one electrically conducting and/or semiconducting zone, being made of a material selected from steel, iron, copper, nickel, cobalt, niobium, aluminium, silver, titanium, silicon, tungsten, tantalum, gold, germanium, platinum, iridium, silicon-aluminium alloy, platinum-aluminium alloy and others alloys comprising at least one of these materials. The selectivity of the aromatic diazonium salt derived polymer also depends on the nature of the electrically conducting and/or semiconducting zone to functionalize, and it appears that the more preferred materials are the silicon, the gold, the silicon-aluminium alloy and the platinum-aluminium alloy.

The electrically conducting and/or semiconducting zone is functionalized with the aromatic salt derived polymer by electrochemical polymerization reduction.

The process for the preparation of the device according to the present invention may comprise the following steps:
  contacting said electrically conducting and/or semiconducting zone of the pair of electrodes of said gas sensor with a solvent comprising at least one aromatic diazonium salt derived polymer as defined according to the present invention, and
  electro-grafting said at least one aromatic diazonium salt derived polymer at the surface of the pair of electrodes of said gas sensor by electrochemical polymerization reduction.

The process consists in binding the aromatic diazonium salt derived polymer of the present invention to the electrically conducting and/or semiconducting zone of the working electrode and the counter electrode of the gas sensor, by placing said electrically conducting and/or semiconducting zone in contact with a solution comprising the diazonium salt in a solvent, and negatively polarizing said electrically conducting and/or semiconducting zone relative to an anode (a reference electrode) which is also in contact with said aromatic diazonium salt solution.

The electrochemical reduction can be represented schematically according to the following mechanism:

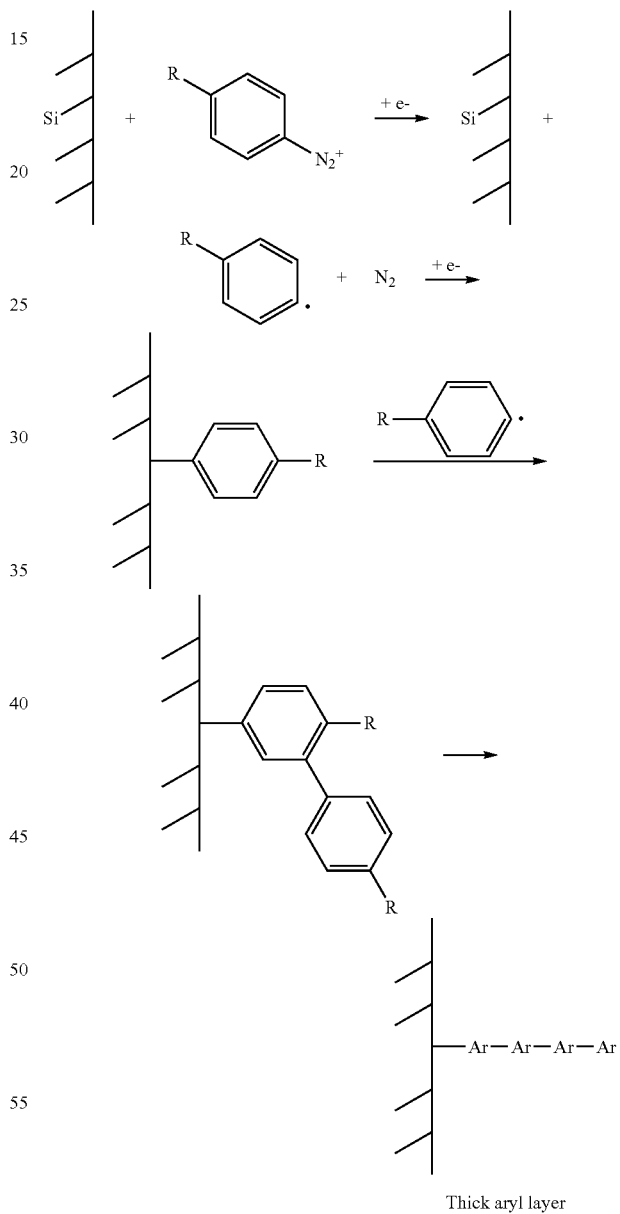

Thick aryl layer

The organic film formed is a polymeric layer constituted by a backbone comprising aromatic cores with pendent —R groups.

The cathode potential is set at a value such that the neutral radical R-A· is not reduced and does not give a carbanion. The potential should thus be adjusted to a value which is not too negative in order to stabilize the neutral radical R·.

In a preferred embodiment, the solvent used in the first step of the process for the preparation of a device according to the present invention may be selected from acetonitrile, dimethylformamide, dimethylsulphoxide, benzonitrile and propylene carbonate, and preferably from acetonitrile and propylene carbonate.

According to another embodiment, the solution comprising the aromatic diazonium salt of the present invention can optionally comprise an electrolyte such as quaternary ammonium salts, alkali metal salts or ionic liquids which are soluble in the medium. Among these salts, mention may be made of quaternary ammonium or alkaline halides, acetates, tetrafluoroborates, perchlorates and hexafluorophosphates, and more particularly lithium tetrafluoroborate and tetralkyl ammonium tetrafluoroborate, such as tetrabutyl ammonium tetrafluoroborate and tetrabutyl ammonium hexafluoroborate. The electrolyte may also be simply an acid chosen from hydrochloric acid, sulphuric acid, nitric acid, nitrous acid, phosphoric acid and tetrafluoroboric acid.

The aromatic diazonium salt concentration in the solvent and the electrolyte concentration in the solvent are generally comprised from $2.10^{-3}$ to $10^{-2}$ mol/L for the aromatic diazonium salt, and from $10^{-2}$ to 1 mol/L for the electrolyte.

By way of example, the organic film of the present invention may be formed electrochemically by immersing a pair of electrodes of a gas sensor with a third electrode (a reference electrode) in a diazonium salt solution as defined above. The current inlet is connected to the working electrode, and all the electrodes are connected to a potentiostat which allows the control of the reaction by cyclic voltametry or amperometry.

The pair of electrodes forms an anode and the reference electrode forms a cathode, thereby to produce the organic film between and in contact with the pair of electrodes. The organic film resulting from the electro-polymerization of said aromatic diazonium salt derived polymer is commonly formed across the working electrode and the counter electrode separated by a narrow gap, the distance between the working electrode and the counter electrode being comprised from few mm to 2 cm.

It is generally preferred that the current is not greater than 1 mA during the production of the organic film, and it is applied during few seconds to few minutes.

The electrically conducting and/or semiconducting zone of the pair of electrodes of said gas sensor may be functionalized with one layer of the organic film of the present invention, the thickness of said monolayer being comprised from 1 to 5 nm. Another possibility according to the present invention consists in functionalizing said electrically conducting and/or semiconducting zone with at least two layers of the organic film of the present invention, the thickness of these at least two layers being comprised from 5 to 50 nm, and preferably from 20 to 30 nm. Polymer thickness is controlled by the time of the electrochemical polymerization reaction. The advantage of thin organic films is the relatively rapid response of the coated gas sensor at low gas concentrations.

According to another preferred alternative, and still according to the invention, the electrically conducting and/or semiconducting zone of the pair of electrodes of said gas sensor comprises at least two different zones functionalized with at least two different aromatic diazonium salts as defined according to the present invention. In this case, the previously described process is twice repeated with an additional washing step, in the solvent used for the polymerization between the two steps. Each of these specific aromatic diazonium salts allows the detection of different specific gases.

Another subject-matter of the present invention is a process for detecting gases and/or volatile organic compounds (VOC) comprising the following steps:
exposing at least one gas and/or volatile organic compound (VOC) to a device as defined according to the present invention,
monitoring the resonance frequency of the gas sensor with a measuring apparatus by placing the resonant sensor element in an electrical oscillator feedback loop that continually excites the sensor into mechanical motion at one of its natural resonance frequencies, that is in turn transduced into an electrical frequency signal,
transmitting the electrical frequency signal of the measuring apparatus to a computer.

Exposure of gases and/or volatile organic compounds produces a variation of the resonance frequency between the electrodes of the gas sensor, which can be measured. Response to these gases is substantially instantaneous at room temperature, the step of contacting a gas or a volatile organic compound (VOC) with the device is performed when the device is placed in a space wherein gas or volatile organic compound (VOC) detection is wanted and a gas or a volatile organic compound (VOC) is introduced into such space, the introduction of the gas being voluntary or not.

According to a preferred embodiment of the invention, said process for detecting gases and/or volatile organic compounds (VOC) may present a partition coefficient $K_p$ between the vapour in the gaseous phase and the polymer in the liquid phase comprised from 200 to 4500, whereas in the state of the art the $K_p$ values are generally comprised from 100 to 1000.

Such devices and processes find applications in any situation where gases detection is needed: in domestic public space or industrial context.

Figure 2:
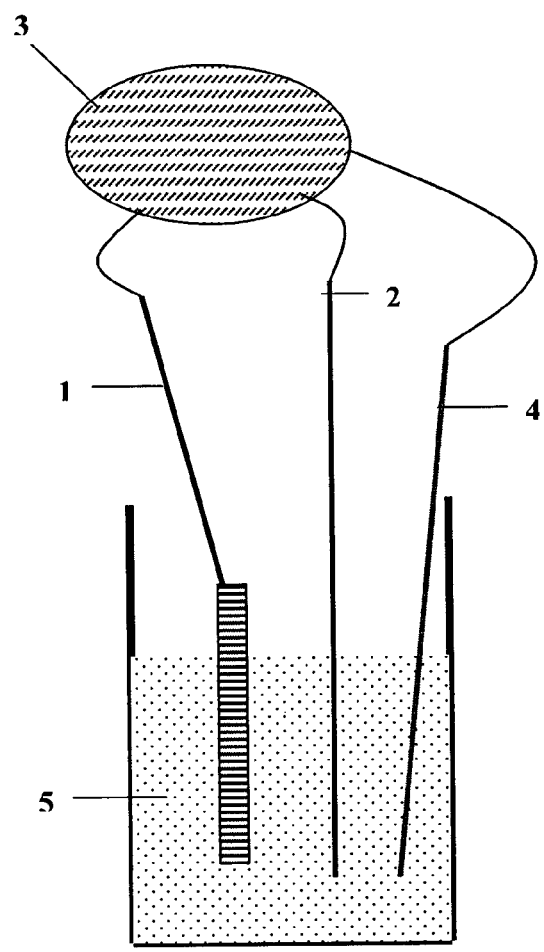
Figure 3:
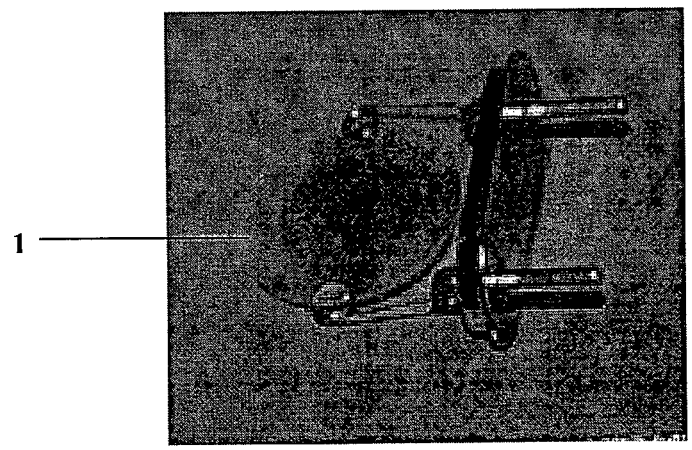
Figure 4:
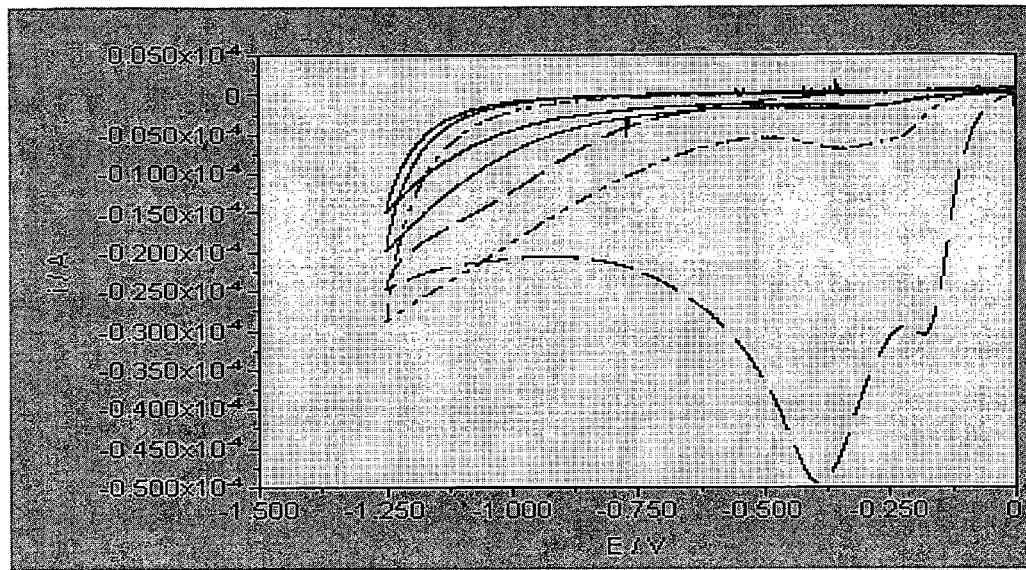
Figure 4:
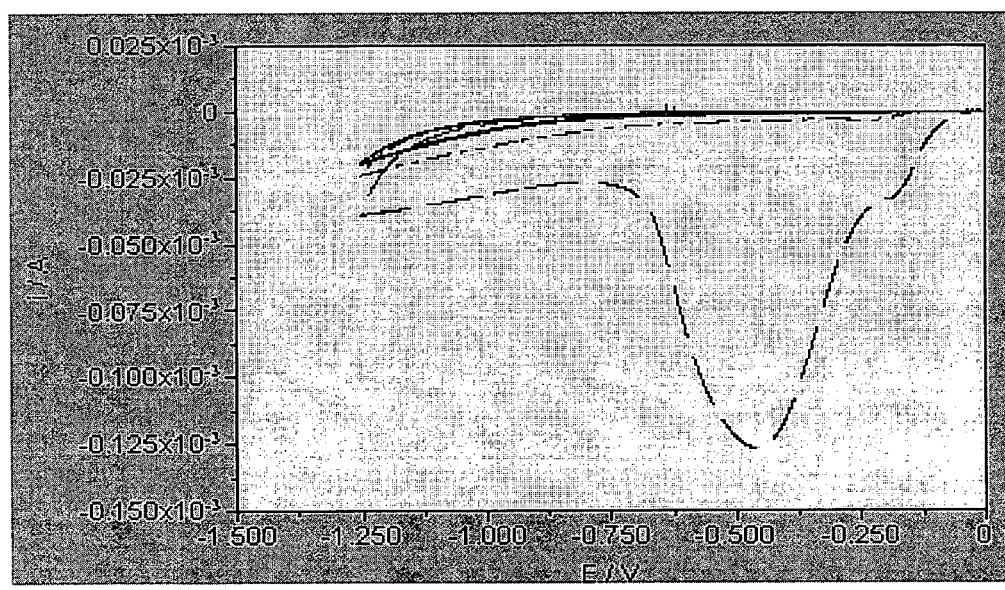
Figure 5:
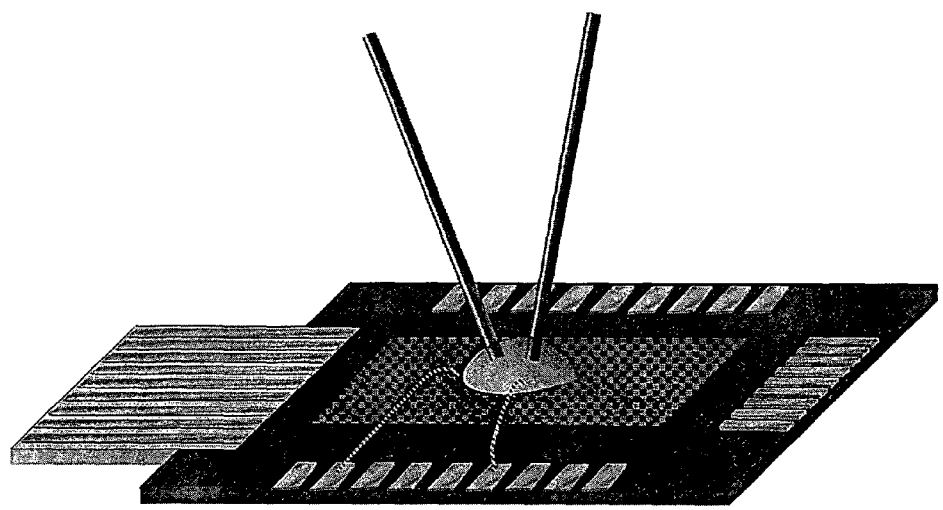
Figure 6:
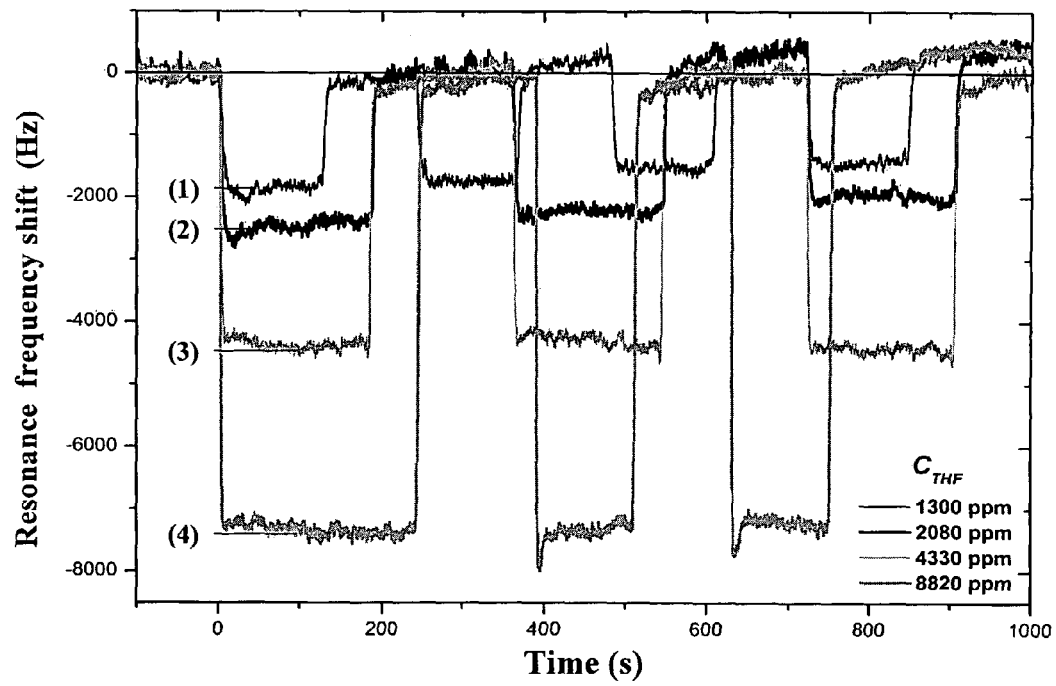

In addition to the above provisions, the invention also comprises other provisions which will become clear from the description which follows, which refers to examples illustrating the technical advantages of the devices according to the present invention, and also to the attached drawings in which:

FIG. 1 shows different geometries of piezoelectric sensors according to the invention: geometries of type NEMS, MEMS and quartz crystal microbalance (QCM), comprising a material 1 which can be a conducting or a semiconducting or an insulating material, a material 2 which can be a conducting or a semiconducting material, and an area of the sensor 3 to functionalize, the current inlet arriving within the sensor in A, in B (face before) or in C (face back), FIG. 2 shows a connecting diagram in which a pair of electrodes (working electrode 1 and counter-electrode 2) of a gas sensor connected to a potentiostat 3, comprising a third electrode (a reference electrode 4), is immersed in a diazonium salt solution 5 according to the invention, FIG. 3 shows a functionalized quartz crystal microbalance (QCM), in which only the Au surface is functionalized, FIG. 4 represents two quartz crystal microbalances (QCM) voltamograms, FIG. 5 shows a NanoElectroMechanical Systems (NEMS), and FIG. 6 shows the resonance frequency of a sensor according to its gaseous environment.

EXAMPLES

Effect of the Nature of the Surface to Functionalize on the Selectivity of the Aromatic Diazonium Salt Derived Polymer Current was applied in silicon, gold and silicon-aluminium alloy electrodes electrically connected to silicon electrodes.

The low part of the device was dipped into the solution to be polymerized containing the 4-bromophenyldiazonium salt, and the polymerization was realized using the same apparatus previously described.

AFM measurements (tapping method) were made before and after the functionalization of the electrically conducting and/or semiconducting surface of the gas sensor, in order to measure the thicknesses of the layers electro-grafted on each surface.

TABLE 1

| Surface of the gas sensor | Thickness of the layer (nm) |
|---|---|
| Silicon | 20 |
| Gold | 30 |
| Silicon-aluminium alloy | 1-2 |

Although the silicon-aluminium alloy is a good conducting material, the electro-grafting on this surface is more difficult than for the silicon and gold materials, as the silicon-aluminium alloy is covered by a passivation layer ($Al_2O_3$) difficult to eliminate, and which recurs during the electro-grafting.

Example 1

Two quartz crystal microbalances (QCM) were functionalized respectively with:

an aromatic diazonium salt derived polymer bearing a —$NO_2$ group: the 4-nitrophenyl diazonium tetrafluoroborate (QCM 1), and an aromatic diazonium salt derived polymer bearing a —Br group: the 4-bromophenyl diazonium tetrafluoroborate (QCM 2).

Both faces of the quartz crystal microbalances (QCM) were functionalized with the aromatic diazonium salt derived polymer.

Only the gold part of the quartz crystal microbalance (QCM) was functionalized, as the central part of the quartz crystal microbalance (QCM) is in quartz and is not electrically active for the electro-grafting.

The polymerization was realized by cyclic voltametry in an acetonitrile solution comprising tetrabutyl ammonium tetrafluoroborate as electrolyte, the concentration of the aromatic diazonium salt being of 4 mol/L.

The voltamograms obtained during the polymerization are represented in FIG. 4.

Bit by bit of the cycles, we observe a decrease of the current indicating the formation of the polymer layer.

After having been functionalized, the quartz crystal microbalance (QCM) sensors were rinsed during 5 minutes under ultrasounds in an acetonitrile solution, in order to eliminate the possible electro-grafted molecules remaining at the surface of the sensors.

Then, the affinity of the coated sensors of the present invention with different kinds of gases was tested, by measuring the modification of the resonance frequency of the quartz according to its gaseous environment.

The results were estimated by calculating the partition coefficient $K_p$ between the sensitive polymer layer and the gaseous phase.

TABLE 2

| Analyte | $K_p$ QCM 1 | $K_p$ QCM 2 | Ratio $K_p$ (QCM 1)/$K_p$ (QCM 2). |
|---|---|---|---|
| Hexane | 760 | 215 | 3.53 |
| Toluene | 3457 | 1175 | 2.94 |
| Ethanol | 3424 | 749 | 4.57 |
| Ethyl acetate | 2624 | 758 | 3.46 |
| Cyclohexane | 936 | 430 | 2.18 |
| n-octane | 4560 | 1463 | 3.12 |
| i-octane | 2212 | 710 | 3.12 |

As mentioned in the description, the higher the value of $K_p$, the more important is the affinity of the molecule with the sensitive polymer layer.

For a given sensitive polymer layer, the value of $K_p$ changes according to the molecule to detect, which indicates that there is a selectivity of the sensitive polymer layer according to the nature of the gases.

We also observe that the ratio $K_p$ (QCM 1)/$K_p$ (QCM 2) is not constant, which demonstrates a selectivity between the different polymer layers tested.

These observations allow us to conclude that the polymer layers of the present invention are interesting to detect, in a sensitive and selective manner, analytes present in gaseous phases.

Example 2

By the same way described in example 1, two NanoElectroMechanical Systems (NEMS) were functionalized respectively with:

an aromatic diazonium salt derived polymer bearing a —$NO_2$ group: the 4-nitrophenyl diazonium tetrafluoroborate (NEMS 1), and an aromatic diazonium salt derived polymer bearing a —Br group: the 4-bromophenyl diazonium tetrafluoroborate (NEMS 2).

NEMS 1 and NEMS 2 have a resonance frequency of 20-21 MHz and a quality factor of respectively 84 and 89.

After bonding, electrografting on NEMS was performed without any additional surface preparation but under an argon atmosphere. NEMS devices were connected to an Autolab PGSTAT100 potentiostat (from Eco Chemie BV) equipped with general-purpose electrochemical system software.

Electrografting is performed in a drop of propylene carbonate containing 0.05 mol/L of tetrabutyl ammonium hexafluorophosphate and $2.10^{-3}$ mol/L of aromatic diazonium salt.

A platinum wire and a silver wire both plunged in the drop are respectively used as auxiliary and pseudo reference electrode.

Cathodic potential sweeps between 0 to −2V using cyclic votammetry conduct to the deposit of the sensing layer.

Further washes with acetonitril are done to eliminate the deposited materials that are not covalently bonded (see FIG. 5).

After chemical coating, the affinity of the coated sensors of the present invention was tested with tetrahydrofuran (THF), by measuring the modification of the resonance frequency of the sensor according to its gaseous environment.

A typical experiment is constituted by a succession of injection of THF. We observed a dependence between the gas concentration and the shift frequency of the sensor, as shown on FIG. 6.

The results were estimated by calculating the partition coefficient $K_p$ between the sensitive polymer layer and the gaseous phase.

TABLE 3

| Analyte | $K_p$ NEMS 1 | $K_p$ NEMS 2 | Ratio $K_p$ (NEMS 1)/$K_p$ (NEMS 2) |
|---|---|---|---|
| THF | 370 | 1430 | 0.26 |

The invention claimed is:

1. A device for detecting at least one gas and/or volatile organic compound (VOC), comprising transduction means and a gas sensor, characterized in that a surface of said gas sensor comprises at least one electrically conducting and/or semiconducting zone functionalized with at least two layers of organic film resulting from a polymerization of at least one aromatic diazonium salt, wherein a thickness of these at least two layers is from 5 to 50 nm; and
wherein the at least one gas and/or the volatile organic compound is detected by measuring a shift in a frequency of mechanical motion of the gas sensor when the at least one gas and/or the volatile organic compound is added on the surface.

2. The device according to claim 1 characterized in that said electrically conducting and/or semiconducting zone of said gas sensor is made of a material selected from: steel, iron, copper, nickel, cobalt, niobium, aluminium, silver, titanium, silicon, tungsten, tantalum, gold, germanium, platinum, iridium, silicon-aluminium alloy, platinum-aluminium alloy and others alloys comprising at least one of these materials.

3. The device according to claim 1 characterized in that said transduction means comprise means for applying electrical signals across electrodes, wherein the organic film is between the electrodes; and
detection means for detecting a chosen electrical signal in the presence of the at least one gas and/or the volatile organic compound.

4. The device according to claim 1 characterized in that said gas sensor is at least one device selected from a surface acoustic wave (SAW) sensor, a bulk acoustic wave (BAW) sensor, and a quartz crystal microbalance (QCM).

5. The device of claim 1, wherein the least one aromatic diazonium salt has the following formula:

in which:
X$^-$ is an anion,
Ar is an aryl group which can be mono-, di-, or trisubstituted with one or more R groups,
R is selected from a hydrogen atom, linear or branched aliphatic radicals comprising from 1 to 30 carbon atoms, aromatic radicals comprising 5 or 6 carbon atoms, aromatic radicals comprising 5 or 6 carbon atoms and 1 to 3 heteroatoms chosen from —N, —O or —S, halogen atoms, carboxyl, nitro, amino, amido, cyano groups, or alkoxy or alkoxycarbonyl groups comprising from 1 to 3 alkoxy units,
m is equal to 1, 2 or 3, and
n is equal to 1, 2 or 3.

6. The device of claim 1, wherein the gas sensor is a Micro ElectroMechanical System (MEMS) sensor or a Nano ElectroMechanical System (NEMS) sensor.

7. The device according to claim 5 characterized in that said substituent —R is selected from: —Br, —COOH, —NO$_2$, —OCH$_3$, —CONH$_2$ and —OCH$_3$.

8. The device according to claim 5 characterized in that said anion X$^-$ is selected from: Cl$^-$, Br$^-$, I$^-$, HSO$_4^-$, ClO$_4^-$, BF$_4^-$, PF$_6^-$, C$_8$H$_{17}$SO$_3^-$, CH$_3$C$_6$H$_4$SO$_3^-$, ZnCl$_4^{2-}$, and Fe(CN)$_6^{3-}$.

9. The device according to claim 5 characterized in that said aromatic diazonium salt of formula (I) is selected from a 4-nitrophenyl diazonium salt, a the 4-bromophenyl diazonium salt, a 4-methoxyphenyl diazonium salt and a fast blue red salt.

10. A process for detecting gases and/or volatile organic compounds (VOC) characterized in that it comprises the following steps:
exposing at least one gas and/or volatile organic compound (VOC) to a gas sensor of a device, wherein the gas sensor comprises at least one electrically conducting and/or semiconducting zone functionalized with at least two layers of organic film resulting from a polymerization of at least one aromatic diazonium salt, wherein a thickness of these at least two layers is from 5 to 50 nm;
monitoring the resonance frequency of the gas sensor with a measuring apparatus by placing a resonant sensor element in an electrical oscillator feedback loop that continually excites the gas sensor into mechanical motion at one of its natural resonance frequencies, that is in turn transduced into an electrical frequency signal; and
transmitting the electrical frequency signal of the measuring apparatus to a computer.

11. The process according to claim 10 characterized in that the partition coefficient $K_p$ of the gas and/or the volatile organic compound (VOC) is from 200 to 4500.

12. The process of claim 10, wherein the at least one aromatic diazonium salt has the following formula:

in which:
X$^-$ is an anion,
Ar is an aryl group which can be mono-, di- or trisubstituted with one or more R groups,
R is selected from a hydrogen atom, linear or branched aliphatic radicals comprising from 1 to 30 carbon atoms, aromatic radicals comprising 5 or 6 carbon atoms, aromatic radicals comprising 5 or 6 carbon atoms and 1 to 3 heteroatoms chosen from —N, —O or —S, halogen atoms, carboxyl, nitro, amino, amido, cyano groups, or alkoxy or alkoxycarbonyl groups comprising from 1 to 3 alkoxy units;
m is equal to 1, 2 or 3, and
n is equal to 1, 2 or 3.

13. A device for detecting a gas, comprising:
an electrode comprising at least two layers of organic film, the organic film comprising an aromatic diazonium salt derived polymer, and the aromatic diazonium salt derived polymer selected to detect a specific gas, wherein a thickness of these at least two layers is from 5 to 50 nm; and
wherein the specific gas is detected by measuring a shift in a frequency of mechanical motion of the electrode when the specific gas is added on the organic film.

* * * * *